United States Patent [19]
Lazzara et al.

[11] Patent Number: 5,320,117
[45] Date of Patent: Jun. 14, 1994

[54] DENTAL FLOSSING MATERIAL WITH LEADER

[75] Inventors: Richard J. Lazzara, 1814 N. R St., Lake Worth, Fla. 33460; Anita H. Daniels, Jupiter, Fla.

[73] Assignee: Richard J. Lazzara, Lake Worth, Fla.

[21] Appl. No.: 989,498

[22] Filed: Dec. 10, 1992

Related U.S. Application Data

[63] Continuation of Ser. No. 818,528, Jan. 9, 1992, abandoned.

[51] Int. Cl.$^5$ .............................................. A61C 15/00
[52] U.S. Cl. ................................................... 132/321
[58] Field of Search ......................................... 132/321

[56] References Cited

U.S. PATENT DOCUMENTS

| | | | |
|---|---|---|---|
| 281,731 | 7/1883 | Schimmel | 132/321 |
| 3,744,499 | 7/1973 | Wells | 132/321 |
| 4,450,849 | 5/1984 | Cerceo et al. | 132/321 |
| 4,832,063 | 5/1989 | Smole | 132/321 |
| 4,986,288 | 1/1991 | Kent et al. | 132/321 |

*Primary Examiner*—John J. Wilson
*Attorney, Agent, or Firm*—Alfred H. Rosen

[57] ABSTRACT

An article of dental floss particularly for hygienic maintenance of titanium abutments which is in the form of a ribbon or an elongated strip of woven or non-woven flexible moisture-absorbent material having adequate strength when wet to resist breaking when pulled back and forth adjacent teeth abutments or implant abutments and over gum tissue and is sufficiently soft when wet to avoid scratching the abutments and cutting into or abrading the gum tissue. A relatively stiff leader at one end of the strip serves to thread the strip between teeth and under bridges and bars.

20 Claims, 1 Drawing Sheet

DENTAL FLOSSING MATERIAL WITH LEADER

This is a continuation of Ser. No. 07/818,528 filed Jan. 9, 1992, now abandoned.

BACKGROUND OF THE INVENTION

This invention relates to dental flossing devices, more particularly to dental flossing devices and materials which are uniquely useful to remove food debris and plaque from the transmucosal regions of implant abutments made of relatively soft materials such as titanium and alloys of titanium or gold that are now in use to support dental restorations on dental implant fixtures, as well as natural tooth roots supporting dental restorations.

Dental flossing devices are used in the daily maintenance of healthy teeth and gums. As currently used to maintain natural dentition, as well as dental restorations supported on natural roots, dental flossing devices are string-like in shape, not unlike heavy threads used to sew fabrics together, which in use are pressed between adjacent teeth until making contact with the gums and then drawn back and forth between and against the confronting tooth roots to physically remove daily accumulations of plaque and food debris from the surfaces of the teeth and tooth roots near and immediately under the gums. Threading devices, faintly resembling tailors' needles, are available to thread these string-like flossing devices between teeth under fixed dental bridges. For a number of reasons the existing dental flossing devices are not satisfactory for use to maintain the health of dental restorations supported on dental implant fixtures. Modern dentistry includes the new technique of implantoloqy. In this new technique a dental implant fixture is placed in the jawbone of a patient in a location where the patient is edentulous and an artificial tooth or crown is supported on that fixture. For the patient who is completely edentulous, or is missing a row of teeth, several implant fixtures may be placed, and a bridge or bridges of joined-together teeth may be supported on them. To achieve this support a component, commonly called an abutment, which extends from the implant fixture in bone through the patient's gum, is used to unite the tooth or crown to the fixture. Bridges supported on implant fixtures may include pontics fixed between teeth that are supported on such abutments. The portion of the abutment which exits the gum is subject to the same rigors as a natural tooth at the gum line, that is, it, too, is exposed to food debris and plaque accumulation, and a program of dental hygiene is imperative to maintain the health of the gums and the jawbone where the implant fixture is installed. In fact, such a hygiene program may be more necessary to the maintenance of an implant-supported dental restoration than for the maintenance of natural teeth, for the reason that if plaque and calculus are permitted to collect on the abutment and under the surface of the surrounding gingivae bacteria will eventually attack the bone tissue surrounding or in contact with the implant fixture, and the union between the fixture and the bone will eventually fail.

Titanium and its alloy TiV6A14 are at the present time the materials of choice for use to make dental implant fixtures and the components used with them, including abutments. Titanium is relatively soft compared with natural tooth enamel, so that a titanium abutment is easily scratched. Scratches on the exposed surface of a titanium abutment provide sites for bacteria to take residence and proliferate, a reason being that a roughened surface will collect even more plaque and calculus than a smooth surface. It is accordingly good dental practice to provide smooth surfaces on abutments and other parts of implant supporting structures which are in contact with the gums and periosteal tissues. A need exists to provide dental flossing devices and materials that can be safely used in a program of dental hygiene for the maintenance of an implant-supported dental restoration.

GENERAL NATURE OF THE INVENTION

This invention provides a new article of dental floss which consists essentially of a flexible elongated strip of a moisture-absorbent material having adequate strength when wet to resist breaking when pulled back and forth under a dental bridge or bar between teeth abutments and over gum tissue and sufficiently soft when wet to avoid scratching the abutments. At the present time the preferred material is a non-woven fabric, for example, a nylon embossed material. As presently preferred, the article has a flat ribbon-like shape the cross section of which is wider than it is thick. One end of the strip is made stiff, and thinner than the remainder, to be used as a leader to thread the strip between abutments under a fixed bridge. These and other objects and features of the invention will become apparent from the following description of a preferred embodiment of it, taken together with the accompanying drawings.

DETAILED DESCRIPTION OF THE DRAWINGS

Figure 1:
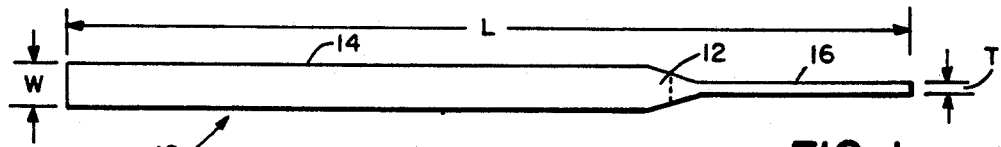
FIG. 1 is a plan view of an article of dental floss.
Figure 2:
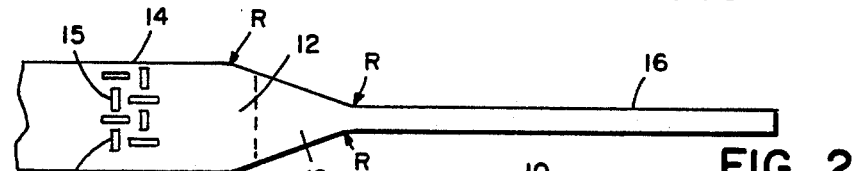
FIG. 2 is an enlarged view of the right-hand portion of FIG. 1.
Figure 3:
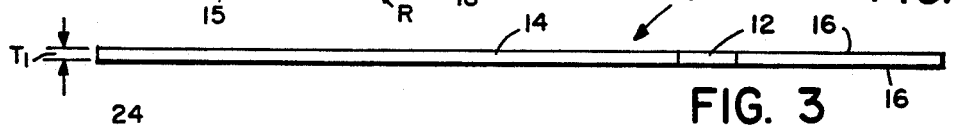
FIG. 3 is an edgewise view of FIG. 1.

The article 10 in FIG. 1 is a strip of length "L" and width "W". At its right-hand end (as seen in the drawings) the strip is narrowed to a width "T" over a leader portion 16 of the length "L". As seen in FIG. 3 the thickness of the strip is "T-1". A transition section 12 intervenes between the major portion 14 of the strip and the leader portion 16. The edges of sections 14 and 16 are curved gradually into the edges of the transition section 12, for example, on radii "R", as is indicated in FIG. 2 sharp edge transitions between adjacent sections of the strip are avoided. The leader portion 16 and an adjoining part 18 of the transition section 12 are made stiff, as by coating or impregnating that portion and part with a thermoplastic nylon adhesive applied by a heat process, which hardens upon cooling.

Figure 4:
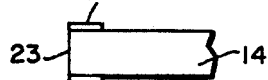
FIG. 4 is an enlarged view of the left-hand portion of FIG. 3.
Figure 5:
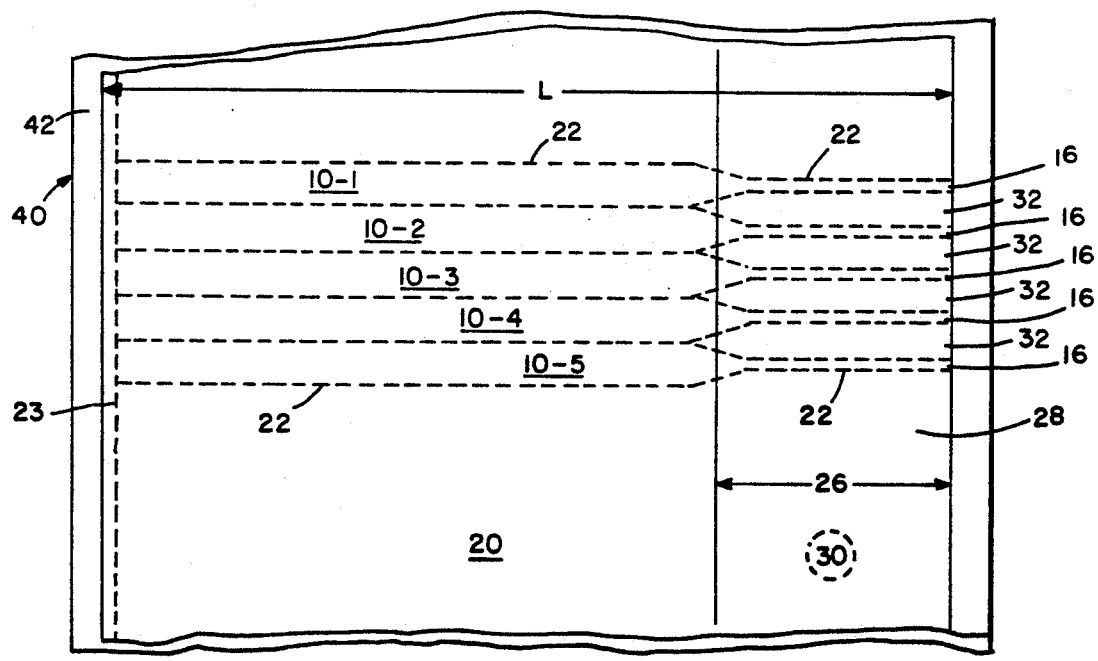
FIG. 5 is a plan view of a group of articles of dental floss joined together at their left-hand ends.

To manufacture the article 10 a web 20 of a suitable starting material, of width "L" and continuous in length, is cut (e.g: die cut) on dashed lines 22 so as to outline a series of articles 10-1, 10-2, 10-3, 10-4, 10-5, etc. extending in a side-by-side along the web. A short part 23 of the left hand edge of the web (as see in the drawing) is left un-cut so that the articles in the series are attached together in that part. As seen in FIG. 4, an adhesive 24, for example, a thermoplastic nylon, is applied along one or both sides of the edge part 23, for a purpose to be described. Prior to cutting the web a band 26 of the web 20 along the right-hand side 28 is coated or impregnated with a hardening material 30; after cutting, the sections 32 between the leader portions 16 are removed. At this stage in its manufacture the cut web shown in FIG. 5 may be attached to a stiff sheet or board 40 along an edge portion 42 by means of the adhesive 24, enclosed in a wrapper (not shown) and delivered to the consumer. In use, the consumer removes one strip 10 at a time from the web 20 by detaching it from the web at the left-hand edge part 23, inserts the leader portion 16 between two teeth under a bridge or bar and draws the soft flossing portion 14 back-and-forth between the teeth and under the bridge or bar, or around an abutment.

The presently preferred material for the web 20 is an available nylon embossed material, embossed, for example, is shown at 15 in FIG. 2, which has good moisture absorbency and has satisfactory strength both wet and dry for the above described intended purposes; at the same time it becomes sufficiently soft when wet so that it will not scratch the abutments or cut into the gums. It is also low in lint, so that it does not leave debris behind after use. The web 20 may be a non-woven material or a woven textile. The thickness T-1 is about 1/16 inch, but this dimension may be varied to adjust the tear strength of the article 10. The width W of the article 10 is preferably in the range from about 3/16 inch to about ⅜ inch. The width T of the leader section 16 is about the same as the thickness T-1. The length L of the finished article 10 is about 8 inches, but this dimension may be increased or decreased as desired for the convenience of the user. The length of the leader section 16 is about 2 inches, for convenience in threading the strip 14-12-16 under a dental bridge or bar. A thermoplastic adhesive which is soft when warm and hardens in cooling can be used as the hardening material 30 to endow the leader section 16 with stiffness sufficient to thread the article 10 under a dental bridge or bar. A practical way to do this is to start with a thermoplastic adhesive that has been pre-coated onto a release paper (not shown) and to apply the adhesive to the band 26 at a temperature high enough to soften the adhesive and drive it into the material of the web 20. Preferably, the band 26 is then similarly treated with additional thermoplastic adhesive on its opposite side, to enhance the stiffness of the leader section 16.

Thermoplastic adhesives suitable for this purpose are commercially available. At the present time a nylon heat seal adhesive which has a flexible firm hand when cool is preferred. The adhesive 24 is a release-type adhesive, similar to the adhesive used in "Post It" note papers. A suitable material for the web 20 is 100% nylon #66, chemically pure, with no bonding agent.

We claim:

1. An article of dental floss comprising a flat flexible elongated strip of a moisture-absorbent material having adequate strength when wet to resist breaking when pulled back and forth adjacent teeth abutments or implant abutments and over gum tissue and sufficiently soft when wet to avoid scratching said abutments and cutting into or abrading gum tissue, said strip having two ends and a shape between said ends in which the width dimension is several times the thickness dimension, a portion of said strip near one end thereof being stiff to facilitate inserting said strip into the space under a dental bridge or bar between teeth and over gum tissue, said stiff portion having substantially the same thickness dimension as the remainder of said strip and being narrowed to a width that is substantially closer to said thickness dimension than to the width of said strip.

2. An article according to claim 1 in which said material is a non-woven fabric.

3. An article according to claim 2 in which said strip is made of a nylon material.

4. An article according to claim 1 in which said strip is made of a nylon material.

5. An article according to claim 1 in which said stiff end is coated within a thermoplastic nylon, which hardens to make it stiff.

6. An article according to claim 1 in which said strip is about eight inches long and said stiff end is about two inches of the length of said strip.

7. An article according to claim 1 in which said narrow stiff end is joined to said wider strip in a transition section which gradually narrows from the wider part of said strip to the narrower stiff end.

8. An article according to claim 7 in which said stiff end is treated with a material to make it stiff, said material extending from the tip of said stiff end to about mid-way on said transition section between said narrower stiff end and said wider part of said strip.

9. An article according to claim 1 in which said material is embossed.

10. An article according to claim 1 in which said strip is embossed on a wide side.

11. An article according to claim 1 having on a flat portion of the other end of said strip a release-type adhesive.

12. A plurality of articles according to claim 11, a carrier having a substantially flat carry-surface, said articles being attached to said carry surface with said adhesive, providing a package of said articles each of which can be individually detached from said carrier.

13. A package according to claim 12 in which said articles are arrayed side-by-side on said carry-surface with said ends bearing said adhesive aligned in a substantially straight line on said carry-surface.

14. An article of dental floss comprising a flat ribbon-like flexible elongated strip of substantially uniform thickness that is embossed on at least one of its wide sides and having a stiff leader attached to one end for the purpose of threading the article under a fixed dental bridge or bar, said leader being narrower than said wide side and joined to the remainder of said strip in a transition section which gradually narrows from the width of said wide side to the narrower width dimension of said leader.

15. An article according to claim 14 made of substantially 100% nylon.

16. An article according to claim 15 which is substantially devoid of bonding agent.

17. An article according to claim 14 in which said leader is treated with a material to make it stiff, said material extending from the tip of said leader to part-way on said transition section.

18. An article according to claim 14 having on a flat portion of the other end of said strip a release-type adhesive.

19. A plurality of articles according to claim 18, a carrier having a substantially flat carry-surface, said articles being attached to said carry-surface with said adhesive, providing a package of said articles each of which can be individually detached from said carrier.

20. A package according to claim 19 in which said articles are arrayed side-by-side on said carry-surface with said ends bearing said adhesive aligned in a substantially straight line on said carry-surface.

* * * * *